United States Patent [19]

Hirschhorn

[11] 4,107,348
[45] Aug. 15, 1978

[54] METHOD OF CONSTRUCTING PORCELAIN-METAL DENTAL RESTORATIONS

[76] Inventor: Leo Hirschhorn, 4200 Hillcrest Dr., Hollywood, Fla. 33021

[21] Appl. No.: 760,634

[22] Filed: Jan. 19, 1977

[51] Int. Cl.$^2$ .......................... A61C 5/10; A61C 13/02
[52] U.S. Cl. .................................. 427/2; 427/376 C; 427/419 C; 427/419 D; 264/19
[58] Field of Search ................... 427/2, 376 C, 419 C, 427/419 D; 264/19, 20, 56, 60

[56] References Cited

U.S. PATENT DOCUMENTS

| 2,768,907 | 10/1956 | Lusby | 427/419 C |
| 3,078,186 | 2/1963 | Tierney | 427/419 C |
| 3,089,787 | 5/1963 | Sattler et al. | 427/376 C |

*Primary Examiner*—Willard E. Hoag
*Attorney, Agent, or Firm*—Charles E. Temko

[57] ABSTRACT

An improved method of constructing porcelain-metal dental restorations characterized in a substantial reduction in the number of baking steps employed, thereby significantly improving the quality of the finished product by reducing the occurrence of "gassing" and reducing labor costs.

4 Claims, No Drawings

METHOD OF CONSTRUCTING PORCELAIN-METAL DENTAL RESTORATIONS

BACKGROUND OF THE INVENTION

With continuous increases in the price of gold in both world and domestic markets, manufacturers of metals used in dentistry have commenced to market non-precious and semi-precious metals as a substitute for high gold content precious metals. These metal alloys materially reduce the cost of raw material, and ultimately, the cost of the completed porcelain-to-metal restoration. The difference in cost of new material can amount to as much as $150 to $200 per ounce. As approximately twelve to fifteen prosthetic teeth can be created per ounce of gold, the effective savings in using cheaper metals will be readily appreciated.

However, unlike gold, the substitute metals are far more chemically reactive than noble metals, and during usual baking procedures involved in the application of multiple coats of porcelain to the prosthetic teeth, gaseous reaction products are formed which tend to separate the bond between the metallic base and the porcelain coatings. This effect, commonly referred to in the art as "gassing" not only mechanically weakens the structure of the restoration, but also presents a cloudy and unacceptable appearance in the finished restoration.

As porcelain is transparent, it cannot be applied directly to the surface of the metallic base of the teeth. The normal practice is to apply one or more opaque coatings in the form of a water suspension of a powdered frit. Because of the difficulty in applying thick coats, it is customary to apply at least two thinner coats with a separate baking operation for each coat. The baking temperature is slightly below the temperature required to completely fire the frit, since additional coatings are subsequently applied which must bond to the opaque layers. However, such baking operations are sufficiently hot to cause some oxidation and accompanying "gassing" in non-precious metals, resulting in cracking or crazing of the applied coatings.

If the baking steps associated with the application of the opaque coatings are eliminated, the opaque coatings, upon drying, do not firmly adhere to the surface of the base metal, and the dried particles thereof are easily dislodged by contact with a tool used for applying subsequent coatings.

SUMMARY OF THE INVENTION

Briefly stated, the invention contemplates the provision of an opaque coating which is mixed with a water or water-alcohol solution of a resinous or synthetic resinous binder employed in lieu of the simple water vehicle used in the prior art method. The vehicle is allowed to evaporate, leaving the binder to adhere the opaque coating or coatings to the base metal, so that subsequent colored porcelain coatings may be applied and baked. During the first subsequent baking operation, the resin is vaporized and partially oxidizes to consume any available free oxygen disposed within the oven which normally incorporates a vacuum pump or other air exhaustion means. The volatilization of the vehicle is adjusted to allow sufficient working time depending upon the number of prosthetic teeth being coated in a given restoration.

An alternate method applies the resinous binder in the form of an aerosol sprayed directly upon the opaque coated restoration.

DETAILED DESCRIPTION OF THE DISCLOSED EMBODIMENTS

In accordance with a preferred embodiment of the invention, I prepare a suitable working vehicle for the opaque coating layers which are applied directly to the exposed surfaces of the base metal surfaces of individual prosthetic teeth. The vehicle consists of an evaporable liquid of varying proportions of alcohol and water, and a small quantity of dissolved resinous binder, most suitably a vinyl chloride resin dispersion of known type, although many other resins are suitable. The following examples are to be considered as illustrative, and by no means exhaustive. In the examples, proportions are by weight per 100 parts.

EXAMPLE 1

Water: 95–97 parts
Vinyl Chloride Resinous Dispersion 3–5 parts

Suitable resins which have been tested with substantially equally effective results are commercially available under the following trademarks:

(a) EXON 605 - (Exxon Corporation)
(b) PLIOVIC M 70 or WO (Goodyear Corporation)
(c) GEON 121, or 222 (Goodrich Corporation)

The vehicle is mixed with known and opaque coatings in powdered frit form, and applied directly to the metallic surfaces of the teeth in normal manner, using a suitable brush or other applicator. Successive coatings are allowed to dry, but no baking operation is employed upon the drying of any coat. With drying, the resin will retain the applied coating particles in position, enabling the subsequent application of as many coats of colored porcelain enamel as may be required to obtain a desired result, each subsequent coating being baked in normal fashion. The normal procedure requires a temperature of between 1300° and 1900° F. for periods ranging from 7½ to 10 minutes. The colored porcelain applications are usually made in three coats, and the resin will normally be volatized during the first baking operation. As the known baking operation is carried out at a reduced atmosphere, and the resin will oxidize at a temperature significantly lower than that of the base metal, the small amount of residual oxygen present is completely consumed by the oxidation of the resin, leaving little if any free oxygen for combination with the metal surface of the teeth.

The remaining steps of applying subsequent coatings of colored porcelain enamel are then completed in known manner. Normally a baking operation is completed at the end of each subsequent coat.

EXAMPLE 2

Proceeding as discussed hereinabove in Example 1, the water is partially replaced by grain alcohol, or other more highly volatile, water miscible solvent. Equal parts of water and alcohol have been found suitable where coating is to be applied to one half dozen or less prosthetic teeth, as contrasted with a complete denture. Evaporation of the vehicle takes place at a much faster rate owing to the greater volatility of the alcohol phase, permitting successive coats to be applied at correspondingly faster rates.

EXAMPLE 3

In lieu of providing a resin carrying vehicle which is mixed with the powdered opaque coating, it is possible to apply the resinous binder as an aerosol coating upon previously applied opaque coatings. Satisfactory results have been obtained using, for example, a conventional aerosol hair-setting spray. The procedure in such case is to apply the opaque coatings using a water or water alcohol vehicle, allowing the same to substantially dry, and to lightly spray the then coated restoration until a satisfactory depth of resinous coating is obtained, which may be as little as 0.0005 inch thick. Because of the rapid volatilization of the carrier, usually Freon 12, drying is practically instantaneous, and the spray may be applied without waiting for the liquid vehicle to completely dry.

Other means of applying a small quantity of a resin binder to the opaque coatings may be employed within the scope of the disclosed invention. For example, a resin solution may be applied using an air brush or similar apparatus.

It will be appreciated that not only is the extensive time normally required for baking the opaque coatings eliminated, but, by using the resin to absorb any residual free oxygen within the oven, the occurrence of gassing and its deleterious effects are substantially eliminated. The binder, therefore serves two purposes, i.e. a means to secure the opaque coatings in situ without baking, and as a means for consuming residual free oxygen during the first baking of the colored porcelain coatings.

I wish it to be understood that I do not consider the invention limited to the precise details set forth in this specification, for obvious modifications will occur to those skilled in the art to which the invention pertains.

I claim:

1. In the method of forming dental restorations including prosethetic teeth having a metallic base, there being at least one particulate opaque ceramic coating applied to said base, and at least one transluscent ceramic coating applied to said opaque coating, the improved step of applying said opaque coating in conjunction with a resinous binder in a volatile vehicle, which upon evaporation of said vehicle binds the particles of said opaque coating to said metallic base in the absence of a separate baking operation.

2. The step in accordance with claim 1, further characterized in the incorporation of said resinous binder directly into said volatile vehicle.

3. The step in accordance with claim 1, further characterized in the application of said binder to a previously applied opaque coating by means of an aerosol vehicle.

4. The step in accordance with claim 1, further characterized in said resin being a vinyl chloride resin dispersion.

* * * * *